(12) United States Patent
Chiklis et al.

(10) Patent No.: US 9,127,048 B2
(45) Date of Patent: Sep. 8, 2015

(54) NUCLEIC ACID AMPLIFICATION CONTROLS

(75) Inventors: Gregory R. Chiklis, Franklin, MA (US); James C. D. Hengst, Getzville, NY (US)

(73) Assignee: ZeptoMetrix Corporation, Buffalo, NY (US)

(*) Notice: Subject to any disclaimer, the term of this patent is extended or adjusted under 35 U.S.C. 154(b) by 854 days.

(21) Appl. No.: 11/929,123

(22) Filed: Oct. 30, 2007

(65) Prior Publication Data
US 2008/0102446 A1 May 1, 2008

Related U.S. Application Data

(62) Division of application No. 09/981,506, filed on Oct. 17, 2001, now abandoned.

(60) Provisional application No. 60/241,038, filed on Oct. 17, 2000.

(51) Int. Cl.
*C12Q 1/68* (2006.01)
*C12N 7/04* (2006.01)
*C07K 14/005* (2006.01)
*C12N 7/00* (2006.01)

(52) U.S. Cl.
CPC ............. *C07K 14/005* (2013.01); *C12N 7/00* (2013.01); *C12Q 1/6888* (2013.01); *C12N 2730/10122* (2013.01); *C12N 2730/10163* (2013.01); *C12N 2740/15022* (2013.01); *C12N 2740/16022* (2013.01); *C12N 2740/16063* (2013.01); *C12N 2740/16222* (2013.01); *C12N 2770/24322* (2013.01); *C12N 2770/24363* (2013.01)

(58) Field of Classification Search
None
See application file for complete search history.

(56) References Cited

U.S. PATENT DOCUMENTS

| | | | |
|---|---|---|---|
| 4,613,501 A | 9/1986 | Horowitz | |
| 5,135,864 A | 8/1992 | Montagnier et al. | |
| 5,547,576 A | 8/1996 | Onishi et al. | |
| 5,552,269 A | 9/1996 | Andrieu et al. | |
| 5,777,095 A | 7/1998 | Barbour et al. | |
| 5,994,078 A | 11/1999 | Rundell et al. | |
| 6,072,086 A * | 6/2000 | James et al. | 568/449 |
| 6,074,825 A | 6/2000 | Rundell et al. | |
| 6,171,777 B1 | 1/2001 | Cook et al. | |
| 6,410,219 B1 | 6/2002 | Cook et al. | |

FOREIGN PATENT DOCUMENTS

| | | |
|---|---|---|
| EP | 0 997 529 A2 | 5/2000 |
| JP | 09-176043 | 9/1996 |
| JP | 10-234362 | 2/1998 |
| JP | 2000-116386 | 8/1999 |

OTHER PUBLICATIONS

Eble et al. Resolution of infection status of human immunodeficiency virus (HIV)-seroindeterminate donors and high-risk seronegative individuals with polymerase chain reaction. Transfusion Jul.-Aug. 1992, vol. 32, No. 6, pp. 503-508.*
Lifson et al. Utility of formaldehyde fixation for flow cytometry and inactivation of the AIDS associated retrovirus. Journal of Immunological Methods 1986, vol. 86, pp. 143-149.*
Sebire et al., "Stability of Human Immunodeficiency Virus RNA in Blood Specimens as Measured by a Commercial PCR-based Assay," J. Clin. Microbiol. 36 (2): 493 (1998).*
Fox et al., "Formaldehyde Fixation," The Journal of Histochemistry and Cytochemistry, vol. 33, No. 8: pp. 845-853 (1985).*
Yagi et al., "The Role of DNase and EDTA on DNA Degradation in Formaldehyde Fixed Tissues," Biotechnic & Histochemistry, vol. 71, No. 3: 123-129 (1996).*
Pollice et al. ("Sequential Paraformaldehyde and Methanol Fixation for Simulatenous Flow Cytometric Analysis of DNA, Cell Surface Protein and Intracellular Proteins," Cytometry 13: 432-444 (1992).*
Grovit-Ferbas et al.; Enhanced Binding of Antibodies to Neutralization Epitopes following Thermal and Chemical Inactivation of Human Immunodeficiency Virus Type 1; Journal of Virology, Jul. 2000, vol. 74, No. 13; pp. 5802-5809.
Shepard et al.; Quantitation of Human Immunodeficiency Virus Type 1 RNA in Different Biological Compartments; Journal of Clinical Microbiology, Apr. 2000, vol. 38, No. 4; pp. 1414-1418.
Norman et al.; Preservation of *Mycoplasma* Strains by Freezing in Liquid Nitrogen and by Lyophilization with Sucrose; Applied Microbiology, Jul. 1970, vol. 20, No. 1; pp. 69-71.
Berry et al.; High-Yield Preparation of Isolated Rat Liver Parenchymal Cells; J. Cell. Biol. (1969), vol. 43; pp. 506-520.
Hart et al.; A comparison of polymerase chain reaction and an infectivity assay for human immunodeficiency virus type 1 titration during virus inactivation of blood components; Transfusion (1993), vol. 33, No. 10; pp. 838-841.
Hilfenhaus et al.; Analysis of human plasma products: polymerase chain reaction does not discriminate between live and inactivated viruses; Transfusion, Sep. 1997, vol. 37, No. 9; pp. 935-940.
Kornman et al.; Nucleic Acid Amplification Testing: The New Infectious Disease Testing Method for Donor Blood; Cancer Control (1999); vol. 6, No. 5; 5 pages.
McDougal et al.; Binding of HTLV-III/LAV to T4+T Cells by a Complex of the 110K Viral Protein and the T4 Molecule; Science (1986), vol. 231; pp. 382-385.
Pugh et al.; Hepatitis B Virus Efficacy Testing: Qualification of an Avian Hepadnavirus In Vitro System That Uses Primary Duck Hepatocyte Cultures; 10th International Symposium on Viral Hepatitis and Liver Diseases; Atlanta, USA, 2000, Abstract No. B139.
Pugh et al.; Infection and Uptake of Duck Hepatitis B Virus by Duck Hepatocytes Maintained in the Presence of Dimethyl Sulfoxide; Viology (1989), vol. 172; pp. 564-572.

(Continued)

*Primary Examiner* — Zachariah Lucas
*Assistant Examiner* — M. Franco Salvoza
(74) *Attorney, Agent, or Firm* — Hodgson Russ LLP

(57) ABSTRACT

The present invention discloses positive control material for nucleic acid amplification based detection of microorganisms in biological samples. The control material comprises purified microorganism that is rendered non-infectious but is amenable to nucleic acid amplification. Also disclosed is a process for making and using the control material.

11 Claims, No Drawings

(56) References Cited

OTHER PUBLICATIONS

Pugh et al.; Susceptibility to Duck Hepatitis B Virus Infection Is Associated with the Presence of Cell Surface Receptor Sites That Efficiently Bind Viral Particles; Journal of Virology, Aug. 1995, vol. 69, No. 8; pp. 4814-4822.

Pugh et al.; Use of Surrogate Models for Testing Efficacy of Disinfectants Against Hepatitis B Virus; American Journal of Infection Control Online, Aug. 1999, vol. 27, No. 4; pp. 373-376.

Reed et al.; A Simple Method of Estimating Fifty Per Cent Endpoints; The American Journal of Hygiene, May 1938, vol. 27, No. 3; pp. 493-497.

Seglen; Preparation of Isolated Rate Liver Cells; Methods Cell Biol. (1971), vol. 3; pp. 29-83.

Guidance for Industry "In the Manufacture and Clinical Evaluation of In Vitro Tests to Detect Nucleic Acid Sequences of Human Immunodeficiency Viruses Types 1 and 2"; Food and Drug Administration, Dec. 1999.

Pierce Chemical Company; Instructions for BMPH; and Imidoester Cross-linkers.

Davison et al.; Quantification of HIV DNA in the brain by PCR: differences between fresh frozen and formalin fixed tissue; Journal of Clinical Pathology, 1996, vol. 49; pp. 425-427.

Balachandran et al.; Vesicular Stomatitis Virus (VSV) Therapy of Tumors; IUBMB Life, 2000, vol. 50; pp. 135-138.

Maddon et al.; The T4 Gene Encodes the AIDS Virus Receptor and Is Expressed in the Immune System and the Brain; Cell, Nov. 7, 1986, vol. 47; pp. 333-348.

McDonnell et al.; Antiseptics and Disinfectants: Activity, Action, and Resistance; Clinical Microbiology Reviews, Jan. 1999, vol. 12, No. 1; pp. 147-179.

Koshiba et al., The effect of formalin fixation on DNA and the extraction of high molecular weight-DNA from fixed and embedded tissues; Pathol. Res. Pract. 189(1): 66-72 (1993)(abstract only).

Noguchi et al., Modified formalin and methanol fixation methods for molecular biological and morphological analyses; Pathol. Int. 47(10): 685-91 (1997)(abstract only).

Tang et al., Inactivation of HIV-1 by trypsin and its use in demonstrating specific virus infection of cells; Journal of Virological Methods, vol. 33, Issue 1-2, pp. 39-46 (Jun. 1991).

* cited by examiner

NUCLEIC ACID AMPLIFICATION CONTROLS

This application is a divisional application of U.S. nonprovisional application Ser. No. 09/981,506, filed on Oct. 17, 2001 now abandoned, which in turn claims priority to U.S. provisional application No. 60/241,038, filed on Oct. 17, 2000, the disclosures of which are incorporated herein by reference.

FIELD OF THE INVENTION

The present invention relates generally to the area of virus detection in biological samples. More particularly, the present invention relates to a composition of matter that can serve as a reliable control in the detection of viruses by nucleic acid amplification methods.

DESCRIPTION OF RELATED ART

The presence of virus, such as the human immunodeficiency virus (HIV), in biological samples is typically identified by indirect methods, i.e., by detecting antibodies directed against a particular virus or a component of the virus. This method of detection is limited in its ability to detect minute amounts of virus because antibodies typically do not develop in detectable levels until after the virus has grown or reproduced considerably inside the body. Thus, for example, in methods of screening blood supplies for transfusion, existing indirect methods may not be adequate to screen infected blood. In an effort to diagnose viral infections at an earlier stage, nucleic acid amplification techniques are being developed for detecting and quantifying viruses in biological samples. Such techniques include, polymerase chain reaction (PCR), transcription mediated amplification (TMA), nucleic acid signal based amplification (NASBA) and ligase chain reaction (LCR). These technologies are useful in the diagnosis of viral infection and to monitor viral load in infected individuals during treatment. Further, these technologies are useful in screening of blood prior to transfusion.

Beginning in the spring of 1999, the American Red Cross and 16 member laboratories of America's Blood Centers began testing donor blood for the human immunodeficiency virus (HIV) type-1 and the hepatitis C virus with a new genetic test designed to detect viral infections in their very early stages. These tests, called Nucleic Acid Testing (NAT), are able to detect small amounts of a virus before the blood donor's body mounts an immune response. The power of NAT is its ability to detect the presence of infection by directly testing for viral genomic nucleic acids rather than by indirectly testing for the presence of antibodies. Furthermore, NAT is much more sensitive than other direct detection methods such as HIV p24 antigen detection assay in that NAT can detect as low as 50 viral particles in clinical specimens. NAT could potentially detect HIV in blood approximately 10 days post-infection. The U.S. Food and Drug Administration (FDA) is strongly encouraging blood banks to begin NAT testing and hospitals to use NAT-screened blood (Kornman et al., 1999, *Cancer Control*, Volume 6, Number 5).

Several commercial NAT kits and services are available for the testing of HIV, hepatitis C virus (HCV) and hepatitis B virus (HBV), such as those marketed by Roche Diagnostics (Indianapolis, Ind.), National Genetics Institute, Inc. (Los Angeles, Calif.), Bayer Corporation (Tarrytown, N.Y.) and Gen-Probe, Inc. (San Diego, Calif.). These kits and testing services employ multistep assays wherein the initial step is extraction or partial purification of the target nucleic acid, followed by amplification and detection of the nucleic acid. The positive controls developed for NAT based detection thus far are: 1) plasma or serum from infected individuals and 2) synthetic and cloned nucleic acids. These controls have several drawbacks. For example, although plasma or serum from infected individuals serves as a full process control for all steps in a diagnostic procedure, it contains infectious substances and is not stable at refrigerator temperatures (2-8° C.). Synthetic or cloned nucleic acids do not serve as controls for the extraction step and are therefore, not full process controls. Moreover, the synthetic and cloned nucleic acids are extremely sensitive to nucleases and therefore require special care in handling. A nuclease resistant "armored RNA" has been developed. However, this armored material is not contained within an intact virus particle and thus does not extract similar to virally infected plasma. Thus, the armored material does not serve as a control for the extraction process and also does not amplify with TMA or LCR.

The Center for Biologics Evaluation and Research (CBER) branch of the FDA has released guidelines for HIV NAT control materials. The guidelines (Guidance for Industry, In the Manufacture and Clinical Evaluation of in vitro Tests to Detect Nucleic Acid Sequences of Human Immunodeficiency Viruses Types 1 and 2, BBS, FDA, CBER, December 1999) provide the FDA's recommendations for the format and performance of controls and calibrators for NAT based kits. According to these guidelines, the control material should act as a full process control, i.e., it should act as a control for all the steps of the sample handling and detection process. Further, under the guidelines, the material should be noninfectious and based on a well-validated microorganism. Accordingly, the ideal control should provide an indication of the steps of ultracentrifugation, extraction, amplification, hybridization, quantitation, and of possible contamination.

Thus, in view of the FDA guidelines and the drawbacks identified with the existing control materials, there is a need in the area of viral detection techniques for the development of positive controls that can serve as full process controls, are stable at refrigerator temperatures, and are safe to handle.

Accordingly, an object of the present invention is to provide a noninfectious positive full process control for detection of microorganisms by nucleic acid amplification techniques.

Another object of the present invention is to provide a method for producing the internal controls of the invention.

Another objective of the invention is to provide a method of screening biological samples for the presence of microorganisms by nucleic acid amplification techniques.

These and additional objectives are satisfied by the present invention which comprises nondisrupted inactivated microorganism particles used as positive control material in nucleic acid amplification detection techniques. The control material is comprised of nondisrupted inactivated microorganism and can be formulated in a stabilized plasma matrix. The control material is noninfectious, stable under nonfrozen storage (such as 2-8° C.) and yields reproducible results in nucleic acid amplification assays. The control material of the present invention can be stored at refrigerator temperatures. Further, since the control material comprises whole microorganism particles, it is run as a full process control and thus is handled and processed exactly the same way as the biological sample being tested. As a full process control, the material can be used in the sample preparation step and carried through the entire detection procedure. The control materials of the present invention, thus, qualify for meeting the FDA guidelines.

SUMMARY OF THE INVENTION

The present invention provides a positive control material, which can serve as a reliable control for nucleic acid amplification techniques. The positive control material of the invention generally comprises a virus or parasite that has been rendered noninfectious, but retains the nuclear components substantially intact so as to be amenable to nucleic acid amplification and detection processes.

Thus, this invention provides a purified microorganism comprising surface proteins and substantially intact nuclear components, wherein one or more surface proteins have been irreversibly modified such that the microorganism is thereby rendered non-pathogenic.

This invention also provides a purified microorganism comprising surface proteins and substantially intact nuclear components, wherein one or more surface proteins have been irreversibly modified by covalent attachment of a compound comprising one or more reactive functional groups to one or more reactive sites on said surface proteins, such that said microorganism is thereby rendered non-pathogenic.

This invention further provides a composition of matter comprising a purified microorganism comprising surface proteins and intact nuclear components, wherein one or more surface proteins have been irreversibly modified such that the microorganism is thereby rendered non-pathogenic, and a liquid matrix that simulates a biological fluid.

This invention also provides a method for producing a non-pathogenic purified microorganism comprising surface proteins and intact nuclear components and irreversibly modifying one or more surface proteins while leaving the nuclear components substantially unmodified, such that the microorganism is thereby rendered non-pathogenic.

This invention also provides a method for detection of a microorganism comprising surface proteins in a biological sample by amplification of nuclear components of said microorganism, which method comprises amplification of the nuclear components of a purified control sample of said microorganism, wherein one or more surface proteins of said control microorganism have been irreversibly modified such that said control microorganism is thereby rendered non-pathogenic.

In addition, this invention provides a kit for analyzing a biological sample for the presence of a microorganism having surface proteins, wherein the kit comprises a positive control composition comprising a purified microorganism comprising surface proteins and intact nuclear components, wherein one or more surface proteins have been irreversibly modified such that the microorganism is thereby rendered non-pathogenic.

Other features and advantages of the invention will be apparent from the following detailed description and claims.

DETAILED DESCRIPTION OF THE INVENTION

This invention provides a purified microorganism comprising surface proteins and substantially intact nuclear components, wherein one or more surface proteins have been irreversibly modified such that the microorganism is thereby rendered non-pathogenic.

The microorganisms contemplated in the practice of the invention are those that are pathogenic, and the detection of which would aid in the detection or treatment of an ailment.

As used herein the term "microorganism" includes any infectious microscopic organism that contains surface proteins which aid or assist in the organism's ability to infect a host. For example, gp120 is present on the surface of the HIV virus and acts as a receptor protein that allows the virus to attach to monocytes and lymphocytes through binding to their CD4 receptors. (Maddon et al., 1986, Cell, 47:333; MacDougal et al., 1986, Science, 231:382; Moore et al., 1993, In J. Bentz (ed.), Viral Fusion Mechanisms, CRC Press, Boca Raton, Fla. In separately preferred embodiments, the microorganism can be a virus or an intracellular parasite. As used herein the term "virus" is meant to include either enveloped or nonenveloped viruses and those containing either RNA or DNA as the nuclear material. Examples include, but are not limited to, the human immunodeficiency virus (HIV), hepatitis A virus, hepatitis B virus, hepatitis C virus, cytomegalovirus, human lymphotrophic virus, Epstein-Barr virus, parvovirus, herpes simplex virus, human herpes virus 8. Examples of intracellular parasites include, but are not limited to, *Chlamydia trachomatis, Chlamydia psittaci, Rickettsia prowazeki, Rickettsia typhi, Rickettsia rickettsi, Rickettsia sibtricus, Rickettsia conori, Rickettsia australis, Rickettsia akari, Rickettsia tsutsugamushi, Coxiella bumeti* and *Rochalimaea quintana.*

For the preparation of the control material of the invention, the desired microorganism can be grown by standard methods. For example, for the HIV virus, methods for growth are disclosed in U.S. Pat. No. 5,135,864, which describes the production and purification of HIV. As an alternative source, microorganism can be isolated from infected biological fluids, such as from the blood from an infected animal. The techniques are similar to those used when purifying virus from cell culture. See Davis et al., Microbiology, 2d Ed. (Harper & Row, 1980). Thus, for example, hepatitis B and C viruses can be purified from the blood of infected individuals by this method. In addition, bulk production of the desired microorganism can be derived from a chronically infected cell lines which are available from, for example, the AIDS Research and Reference Reagent Program of the National Institutes of Health (NIH) and the American Type Culture Collection (ATCC).

Once sufficient culture material is available, the microorganism can be purified using techniques known to those of ordinary skill in the art. A typical method of purification is as follows. The first step in purification of microorganisms involves the removal of cells and cell debris. This can be achieved by separation techniques based on size or mass, such as filtration or low-speed centrifugation. Following this, the microorganism can be concentrated by filtration using a suitable pore size or high speed centrifugation to form a partially purified microorganism preparation. The partially purified preparation can then be subjected to ultracentrifugation and density gradient purification techniques to obtain a purified microorganism preparation. The bulk purified material obtained following purification is generally stored at −70° C. and may be tested for viral or parasitic activity by culture techniques, and for nucleic acid integrity by amplification techniques according to methods known in the art or as described herein.

After purification, the microorganism is rendered non-pathogenic according to the methods of this invention by selective modification of its surface proteins whereby the microorganism is rendered non-infectious while the nuclear components are left substantially intact. Thus, the invention provides a method for producing a nonpathogenic microorganism which comprises providing a purified microorganism comprising surface proteins and intact nuclear components and irreversibly modifying one or more surface proteins while leaving the nuclear components substantially unmodified, such that the microorganism is thereby rendered non-pathogenic.

As used herein, the term "substantially intact" allows for minimal contact of the microorganism's intracellular components with the modifying agents so as to preserve enough of the nuclear contents, in particular the nucleic acid content of the cell, from degradation by the modifying reagents such that the nucleic acid is amenable to the nucleic acid amplification techniques discussed herein. As used herein, the term "non-pathogenic" means that as a result of the modification of the surface proteins according to the methods of the invention, the microorganism is not able to infect cells, replicate or cause disease despite having its nuclear contents substantially intact.

In a preferred embodiment of the invention, the purified microorganism is modified by covalent attachment of a compound comprising one or more reactive functional groups to one or more reactive sites on the surface proteins, such that the microorganism is thereby rendered non-pathogenic. As used herein, the "compounds" used are those capable of covalently conjugating to a surface protein or cross-link two or more surface proteins on the microorganism. Surface proteins typically contain several reactive sites at which covalent attachment of compounds and crosslinking are feasible. For example, amine groups can be modified by acylation; sulfhydryl groups can be modified by addition reactions and alkylations; carbonyl and carboxyl groups can be modified by acylation; and aldehyde and hydroxyl groups can be modified by amination and reductive amination. One or more of these modification reactions can be used in the preparation of the non-pathogenic microorganisms of the invention.

According to this embodiment of the invention, surface protein modification generally involves covalent binding to the protein via reactions with exposed amino acid residues. Although any type of covalent modification or crosslinking known to those skilled in the art may be used, it is preferable to use covalent modification or crosslinking of amino, sulfhydryl, and carboxylic acid residues. For example, crosslinking agents that modify the amine groups include gluteraldehyde and paraformaldehyde. Each of these are readily attacked at pH>7 by the nucleophilic free amines from either the protein terminus or by internal lysine side residues. The resultant product is a Schiff's base with a free amine of the protein. Gluteraldehyde is also attacked specifically by these reactive amine residues and leads to a high degree of cross linking.

Suitable reagents for modification of proteins through their sulfhydryl residues are the irreversible sulfhydryl blocking agent N-ethylmaleimide (NEM) or an n-substituted bismaleimide crosslinker. NEM is an alkylating reagent that reacts with sulfhydryl bonds forming a stable thioether bond. This reaction may be carried out at pH 6.0 to prevent reaction with free amines. Other sulfhydryl reactive reagents such as bismaleimidohexane (BMH) may also be used. BMH is a homobifunctional crosslinker with a six carbon spacer between active sites. This cross linker also forms a stable thioether bond at pH 7.0.

In separately preferred embodiments, the chemical modifying agents that can used include monofunctional crosslinkers, which contain a single reactive functional group, such as an aldehyde group. Examples of agents containing aldehyde functional groups include, but are not limited to, formalin (formaldehyde), acetaldehyde, propionaldehyde, n-butyraldehyde, benzaldehyde, p-nitrobenzaldehyde, p-tolualdehyde, salicylaldehyde, phenylacetaldehyde, 2-methylpentanal, 3-methylpentanal and 4-methylpentanal. Alternatively, the chemical modifying agents may include functional groups such as NHS imidate, imidoester, maleimide, chloroacetyl, fluoroacetal, iodoacetyl, bromoacetyl, amine, hydrazide, carbodiimide, and derivatives of these groups. In a preferred embodiment the chemical modifying agent will comprise two or more of such reactive functional groups so as to facilitate multiple covalent attachment with reactive sites on a single surface proteins or crosslinking of separate surface proteins. Compounds containing two same functional groups are referred to herein as having homobifunctional structure and those containing two different functional groups are referred to as having heterobifunctional structure. Particularly preferred homobifunctional reagents include dialdehydes such as paraformaldehyde, glyoxal, malondialdehyde, succinialdehyde, adipaldehyde, gluteraldehyde and phthaldehyde.

Several preferred cross linking and bifunctional conjugating agents useful in the practice of this invention are commercially available from Pierce Chemical Company and can be used according to the methods described in the available product literature, the contents of which are incorporated herein in their entirety to describe the state of the art. Examples of such compounds and general methods are as follows.

N-(β-Maleimidopropionic acid) hydrazide (BMPH) (Pierce Chemical Co., Product No. 22297). BMPH is a sulfhydryl-reactive and carbonyl-reactive heterobifunctional reagent. The hydrazide group can be covalently coupled to carbohydrate residues in glycoproteins and other glycoconjugates after oxidation to produce aldehydes. Sugar groups can be oxidized either by the use of specific oxidases (such as galactose oxidase) or by the use of sodium periodate. Treatment of glycoproteins with 1 mM sodium periodate at 0° C. oxidizes sialic acid groups to possess carbonyls. Reaction with 10 mM sodium periodate at room temperature (RT) will create aldehydes on all sugars containing diols. The reaction of BMPH with these aldehydes creates hydrazone linkages. The maleimide end of the crosslinker can be reacted with sulfhydryl groups on surface proteins. If sulfhydryls are not present, they may be created through disulfide reduction or through thiolation with 2-iminothiolane or SATA. Maleimides react with sulfhydryl groups at a pH of 6.5-7.5, forming stable thioether linkages. Maleimide reaction is typically complete in 2 hours at RT or in about 4 hours at 4° C.

1-Ethyl-3-(3-Dimethylaminopropyl)carbodiimide Hydrochloride (CAS # 25952-53-8) (EDC) (Pierce Chemical Co. Product Nos. 22980, 22981), EDC reacts with a carboxyl group first and forms an amine-reactive intermediate, an O-acylisourea. In two-step conjugation procedures using aqueous solutions, stabilization of the intermediate is achieved using N-hydroxysuccinimide. Reaction with an amine will result in hydrolysis of the intermediate, regeneration of the carboxyl, and release of an N-substituted urea. A side reaction is the formation of an N-acylurea, which is usually restricted to carboxyls located in hydrophobic regions of proteins.

Imidoester crosslinkers (Pierce Chemical Co. Product Nos. 20660, 20663, 21667, 21666, 20700, 20665). Homobifunctional imidoesters possess two identical groups which can react with primary amine groups to form stable covalent bonds. These include dimethyl adipimidate (DMA), dimethyl pimelimidate (DMP), dimethyl suberimidate (DMS) and dimethyl 3,3'-dithiobisproprionimidate (DTBP). Unlike other coupling chemistries, imidoesters have minimal cross-reactivity toward other nucleophilic groups in proteins. In mildly alkaline pH's (7-10), imidoesters react only with primary amines to form imidoamides. Inidoester conjugation is usually performed between pH 8.5-9.0. Imidoesters have an advantage over other crosslinking reagents since they do not affect the overall charge of the protein. They carry a positive charge at physiological pH, as do the primary amines they replace. Imidoester reactions are carried out at 0° C. or room temperature because elevated temperatures can contribute to poor yields with these reactions. Homobifunctional imidoesters are available with varying distances between the groups for different crosslinking needs (e.g., to measure inter-residue distances of proteins and macromolecular complexes and near neighbor relationships between proteins). DTBP, a thiol-cleavable, homobifunctional crosslinker, is used in conjunction with the non-cleavable forms of these crosslinkers to study near neighbor relationships. DMP has been used to crosslink antibodies to Protein A immobilized on an agarose support.

N-hydroxysuccinimide esters (NHS-esters) (Pierce Chemical Co. Product Nos. 21555, 21580, 21655, 21658, 22311, 22312, 22416, 22317, 22309, 22324, 22307, 22308). Disuccinimidyl suberate (DSS) is a water-insoluble, homobifunctional NHS-ester; Bis(sulfosuccinimidyl) suberate (BS3) is its water-soluble analog. These crosslinkers are non-cleavable and widely used for conjugating radiolabeled ligands to cell surface receptors. Additional examples include maleimide species such as m-Maleimidobenzoyl-N-hydroxysuccinimide ester (MBS), m-Maleimidobenzoyl-N-hydroxysuccinimide ester (sulfo-MBS), succinimidyl 4-[γmaleimidophenyl]butyrate (SMBP), sulfosuccinimidyl 4-[p-maleimidophenyl]butyrate (sulfo-SMBP), N-[γmaleimidobutyryloxy]succinimide ester (GMBS), N-[γmaleimidobutyryloxy]sulfosuccinimide ester (sulfo-GMBS), N-[ε-maleimidocaproyloxy]succinimide ester (EMCS), and N-[εmaleimidocaproyloxy]sulfosuccinimide ester (sulfo-EMCS) have maleimide groups.

Primary amines are principal targets for NHS-esters. Accessible α-amine groups present on the N-termini of peptides and proteins react with NHS-esters. However, ε-amines are seldom available on a protein, so the reaction with side chains of amino acids becomes important. While five amino acids have nitrogen in their side chains, only the E-amine of lysine reacts significantly with NHS-esters. A covalent amide bond is formed when the NHS-ester conjugation reagent reacts with primary amines. The reaction results in the release of N-hydroxysuccinimide.

NHS-ester crosslinking reactions are most commonly performed in phosphate, carbonate/bicarbonate, HEPES and borate buffers. Other buffers can also be used provided they do not contain primary amines. Primary amines are found in the structure of Tris, making it an unacceptable buffer for NHS-ester reactions. A large excess of Tris at neutral-to-basic pH can be added at the end of the reaction to quench it. Glycine is a primary amine that can be used in a similar manner.

NHS-esters can be broadly grouped into two separate classes with essentially identical reactivity toward primary amines, water-soluble and water-insoluble forms. Water-soluble NHS-ester solubility is due to the sulfonate (—SO$_3$—) group on the N-hydroxysuccinimide ring. Sulfonated NHS-ester crosslinking reagents are supplied as sodium salts and are soluble in water to a concentration of 10 mM.

The non-sulfonated forms of N-hydroxysuccinimide ester conjugation reagents are not water-soluble. These compounds are first dissolved in an organic solvent then added to the aqueous reaction mixture. Water-insoluble NHS-ester crosslinkers do not possess a charged group. They are lipophilic and therefore membrane-permeable. They are useful for intracellular and intramembrane conjugation.

Water-insoluble NHS-esters can be dissolved in an organic solvent such as DMSO or DMF. The cross linker solution is then added to the aqueous reaction mixture so that the final volume contains up to 10% organic solvent. Crosslinkers begin to fall out of solution at high concentrations as noted by the appearance of a milky, turbid solution. While crosslinking still may occur under such conditions, the protocol may be modified to ensure complete dissolution of the NHS-ester. For example, the aqueous phase can be supplemented with additional organic solvents.

The maleimide group is most selective for sulfhydryl groups when the pH of the reaction mixture is kept between 6.5 and 7.5. At pH 7, the rate of reaction of maleimides with sulfhydryls is 1000-fold faster than with amines. Above this pH range, the reaction rate with primary amines becomes more significant. Maleimides do not react with tyrosines, histidines or methionines as do iodoacetamides. A stable thioether linkage between the maleimide group and the reacted sulfhydryl is formed, which cannot be cleaved under physiological conditions. Hydrolysis of maleimides to a non-reactive maleamic acid can compete with thiol modification, especially above pH 8.0. Hydrolysis can occur prior or subsequent to thiol conjugation.

β-mercaptoethanol, dithiothreitol, mercaptoethylamine, cysteine, and other thiol compounds must be removed prior to coupling. Excess maleimides can be quenched at the end of the incubation period by the addition of free thiols such as cysteine or β-mercapto-ethanol. EDTA can be included in coupling buffer to prevent the reoxidation of disulfides.

1,4-bis-Maleimidobutane (BMB) (Pierce Chemical Co. Product No. 22331). BMB is an intermediate length sulfhydryl-reactive homobifunctional crosslinker. The maleimide ends of the crosslinker can be reacted with sulfhydryl groups on surface proteins. If sulfhydryls are not present, they may be created through disulfide reduction or through thiolation with 2-iminothiolane or SATA. Maleimides react with —SH groups at a pH of 6.5-7.5, forming stable thioether linkages. Maleimide reaction is complete in 2 hours at room temperature or about 4 hours at 4° C.

Following reaction with the crosslinking or conjugating agent, the reaction is quenched by using a suitable agent such as one having the same active group as that contained in the reactive group that is being covalently modified. For example, glycine may be used for quenching crosslinking with paraformaldehyde.

The purified virus can also be inactivated by conjugation of amino acids to carboxylic acid residues on the protein. An example of a conjugating agent is sodium periodate which oxidizes carbohydrate hydroxyl and terminal carboxylic acids on the protein to form active aldehyde intermediates. This activated group is then exposed to a nucleophile at elevated pH in the form of glycine or lysine, which results in an irreversible conjugation of the amino acid to the protein. Variation of coupling time, temperature, and rocking speed to optimize the coupling protocols is well within the purview of those skilled in the art.

In a separately preferred embodiment, the microorganism can be rendered non-pathogenic by enzyme digestion of the surface proteins by commercially available methods. Enzymes that can be used for surface protein modification include, but are not limited to, bromelin, chymotrypsin, clostripain, collagenase, elastase, ficin, kallikrein, metalloendopeptidase, proteinase, aminopeptidase, carboxypeptidase, factor Xa, papain, chymopapain, pepsin, *staphylococcus aureus* protease (V-8 strain), trypsin, either alone or in combination. In this aspect of the invention, the microorganisms are reacted with enzyme preparations in a reaction mixture under conditions and for a period of time sufficient to at least partially digest the surface proteins of the microorganism to render it non-pathogenic, yet retain the nucleic acid content of the microorganism substantially intact. Methods of preparing enzyme solutions for such reactions and methods of carrying out the reactions are known to those of ordinary skill in the art and guidance can be found in such texts as The Worthington Enzyme Manual (Worthington Biochemical Corporation).

Choice of any particular enzyme may depend on such factors as availability, ease of use and substrate specificity, each of which can be assessed by those of ordinary skill in the art. Reactions can be controlled by length of time the microorganism is exposed to the enzyme or by quenching reactions with enzyme inhibitors. For example, Papain, and similarly chymopapain, hydrozyzes a number of peptide and ester bonds and is activated for example by cysteine, sulfide, and sulfite and is inhibited by addition of reagents such as sulfhydryl reagents including heavy metals, carbonyl reagents, and ascorbic acid. Chymotrypsin, an endopeptidase, readily acts on amides and esters of susceptible amino acids, has specificity for bonds involving aromatic amino acids, and catalyzes hydrolysis of bonds of leucyl, methionyl, asparaginyl, and glutamyl residues. The enzyme is inhibited for example by heavy metals, and organophosphorus compounds. Trypsin, a proteolytic enzyme, catalyzes the hydrolysis of peptide bonds between carboxy group of arginine or lysine and the amino group of another amino acid, and is inhibited for example by organophosphorus compounds, benzyl 4-guanidiobenzoate, and 4'-nitrobenzyl 4-guanidinobenzoate. Pepsin is an endopeptidase that catalyzes the hydrolysis of a variety of peptide bonds and is inhibited by phenylacyl bromides, aliphatic alcohols, and diphenyldiazomethane.

The virus material that has been inactivated by the above procedure is separated from the other materials present in the final reaction mixture. This may be achieved by standard techniques of purification including, but not limited to, dialysis, gel filtration and tangential filtration. The final purified, inactivated preparations may be tested for the presence of active viruses by methods known to those of ordinary skill in the art. A convenient method of testing for active viruses is to test for the ability of the virus to replicate. For HIV, for example, this may be done by monitoring the production of HIV p24 antigen in culture media. The purified, inactivated microorganisms of the present invention can be stored at nonfrozen temperatures, such as from 2-8° C.

The invention further provides a composition of matter comprising purified microorganism comprising surface proteins and intact nuclear components, wherein one or more surface proteins have been irreversibly modified such that the microorganism is thereby rendered non-pathogenic, and a liquid matrix. Thus, when prepared as a positive control material, the purified, inactivated microorganism is preferably suspended in a liquid matrix comprising stabilized biological fluids which correspond to fluids from which biological samples will be analyzed. Such fluids include, but are not limited to, serum, plasma, defibrinated plasma, stabilized plasma pool, cerebral spinal fluid (CSF), urine, saliva, semen, and sputum. Alternatively the liquid matrix can comprise synthetic matrices formulated to simulate such biological fluids. Methods of preparing synthetic biological fluids are well known in the art. Further, the liquid matrix can contain additives such as antioxidants, buffer salts, preservatives, antibiotics, and matrix stabilizing fillers such as sugars (monosaccharides and polysaccharides), proteins (including albumin, ovalbumin, gamma globulin, red blood cell lysates, casein, dry powdered milk, and/or other serum proteins), and synthetic stabilizers such as poly-vinylpyrrolidine, poly-1-lysine, and methylated Bovine Serum Albumin (BSA). The liquid matrix can also be modified for lyophilization for long term storage and stability by addition of, for example, sucrose and mannose.

In addition, this invention provides a kit for analyzing a biological sample for the presence of a microorganism having surface proteins, wherein the kit comprises a positive control composition comprising a purified sample of said microorganism comprising surface proteins and substantially intact nuclear components, wherein one or more surface proteins have been irreversibly modified such that the microorganism is thereby rendered non-pathogenic. In a preferred embodiment, the kit comprises the non-pathogenic microorganism control in a liquid matrix as described above. In the practice of the invention, the kit can comprise additional materials necessary for conducting nucleic acid amplification techniques known to those of ordinary skill in the art. Further, the invention is intended to encompass the addition of the non-pathogenic microorganism of the invention to existing kits and services used in nucleic acid amplification techniques. Such kits and services include, but are not limited to, those marketed by Roche Diagnostics (Indianapolis, Ind.) under the COBAS AMPLICOR tradename and the NAT screening services marketed by National Genetics Institute, Inc. (Los Angeles, Calif.) Bayer Corporation (Tarrytown, N.Y.) and Gen-Probe, Inc. (San Diego, Calif.).

The non-infectious, inactivated control material of the present invention serve as a positive control for the entire process of nucleic acid amplification techniques. For example, the control material of the present invention comprising inactivated HIV virus can be processed through the steps of (1) sample preparation (chaotrophic salt/solvent extraction), (2) reverse transcription of RNA to produce cDNA if necessary, (3) amplification of the nucleic acids and (4) detection of amplified nucleic acids.

Thus the invention also provides a method for detection of a microorganism comprising surface proteins in a biological sample by amplification of nuclear components of said microorganism, which method comprises amplification of the nuclear components of a purified control material of this invention. In a preferred embodiment, the method comprises the steps (a) preparing a sample by addition of the non-pathogenic microorganism control of the invention to a biological sample to be tested for the presence of a corresponding microorganism, (b) extracting target nucleic acid to be amplified, (c) amplifying target nucleic acid, (d) hybridizing the amplified target nucleic acid with detectably labeled nucleic acid probes, and (e) detecting the hybridized amplified target nucleic acid. Such individual method steps are well known to those of ordinary skill in the art. For example, amplification of target nucleic acid can be accomplished by polymerase chain reaction (PCR) on DNA or on RNA after reverse transcription of the RNA to cDNA. Hybridization and detection can be accomplished by use of, for example, alkaline phosphatase-labeled nucleic acid probes, or by detection of amplicons with energy transfer methodology. In a particularly preferred embodiment, the method can further comprises quantification of the target nucleic acid contained in the biological sample.

In the practice of the invention, the method can be used as a screening method, such as to screen biological fluids prior to transfusion or transplantation, a diagnostic tool, such as where biological fluids from individuals suspected of harboring pathogenic microorganisms are analyzed for the presence of such microorganisms, or as a therapy monitoring tool, such as where biological samples from a patient undergoing treatment for infection is analyzed for presence and amount of microorganism.

The various embodiments and advantages of the present invention will be better understood from the examples presented below, which are intended to be illustrative and not restrictive.

EXAMPLE 1

This example describes the large scale manufacture of purified HIV particles. A chronically infected cell line, designated BP-1, was used to provide the virus. This cell line is a high producing variant of the original H-9 cell line and was provided by Dr. Bernard Poiesz. The cell line was maintained in RPMI-1640 medium supplemented with FBS and antibiotics (penicillin and streptomycin). Master Cell Banks (MCB) and Working Cell Banks (WCB) of each cell line were established and maintained according to accepted USFDA guidelines for manufacture of biologics. Typically, a MCB has 30 to 50 vials of frozen cells. A vial of the MCB is thawed, grown in culture and used to prepare 30 to 50 vials of frozen cells that constitute the WCB. MCB and WCB are stored in secure liquid nitrogen containers and logs are maintained to ensure traceability.

For HIV manufacturing, a WCB vial of a cell line was thawed and expanded in culture containing RPMI-1640, fetal bovine serum (PBS) and antibiotics. Initially, the cells were grown in static cell culture flasks until a volume of 1 liter was reached. At this point the cells were transferred to 2 liter roller baffles, containing 1 liter of culture fluid per bottle, and were expanded further to reach a production scale of 60 to 70 roller bottles. Roller bottle cultures were maintained according to written Standard Operating Procedures and routine testing was done to check for mycoplasma and other adventitious agents.

Once the cultures reached production scale, the roller bottles were harvested once per week. Typically, 90% of each culture was harvested, however, this may vary slightly according to cell density at the time of harvest. Harvested cell cultures were processed in a dual flow path tangential flow system consisting of two filtration loops. The first loop used a 10 square foot 0.45 um membrane to remove cells and cell debris and the second flow path uses a 10 square foot 300 Kd cut off membrane to concentrate the virus containing culture supernatants. The system was washed twice with tris buffered saline and virus containing supernatants were concentrated to approximately 2 liters.

Virus was isolated from concentrated supernatants by ultracentrifugation (30,000×g). Pelleted virions were resuspended in 50 ml of tris buffered saline. This material was then loaded onto a 1.2 liter 22-66% linear sucrose gradient and virus was purified by density gradient ultracentrifugation. Virion containing gradient fractions were identified by refractive index and pooled fractions were diluted in tris buffered saline and virions were again pelleted. Virions were then resuspended in phosphate buffered saline.

All manufacturing activities involving growth and purification of viable viruses were conducted in Biological Level 3 (BL-3) laboratories. Liquid wastes generated by these procedures were treated with hypoclorite or activated iodine before discharge into municipal sewage. Solid wastes were treated by autoclaving before being removed from the BL-3 laboratories.

EXAMPLE 2

This example describes one method of inactivation of the purified virus according to the invention by crosslinking of surface proteins. As an illustration, the crosslinking of virion envelope proteins with paraformaldehyde, a commonly used fixative for tissue and cell preparation, was tested. Titrations of the fixative were preformed above and below the concentration recommended by the CDC for inactivation of virus in biological fluids (May 8, 1992/41 (RR-8); 001 CDC Guidelines for the Performance of CD4+ T-Cell Determinations in Persons with Human Immunodeficiency Virus Infection). Initially, purified virus was slowly thawed at 2-8° C. for 6-8 hours to minimize lysis of the virus. Next, while on ice, virus was diluted with cold PBS to a final concentration of approximately $1 \times 10^{10}$ copies/mL (cp/mL). Diluted virus was then divided into four different 5 ml aliquots and freshly prepared paraformaldehyde was added to each at a final concentration of either 0.625, 1.25, 2.5, or 5%. The reaction mixtures were then incubated at 2-8° C. for 60 minutes while gently rocking. To quench the reaction, 1 mL of 0.5 M glycine (pH 7.4) was added and allowed to react with any residual paraformaldehyde. After the addition of glycine the reactions were gently rocked for 2 hr. at 2-8° C. To remove glycine and any excess unquenched fixative each reaction mixture was then dialyzed (10-14K m.w. cutoff) against IL PBS (pH 7.4, 2-8° C.) for 4 changes. Dialyzed virus was then transferred into a 15 mL tube and centrifuged for 10 min. at 3,000×g to pellet any precipitated virus. A sample of each supernatant was then tested in cell culture for the presence of infectious virus.

The remaining inactivated virus was titrated into a stabilized plasma matrix that consisted of the following: human source plasma collected in 4% Sodium Citrate, 1 mL EDTA, 1 U/mL Ribonuclease Inhibitor (Human Placenta), 0.09% $NaN_3$, 1 mM Dithiothreitol, 0.05% Gentamicin, in Phosphate Buffered Saline pH 7.4. In order to optimize the matrix for other viruses, one or more of the additives can be deleted.

EXAMPLE 3

The modified virus produced as described in Example 2 was tested to ensure the process inactivated the virus. As an illustration, the CEM cell line, obtained from the American Type Culture Collection was used as a host cell for viral infectivity studies. Advantages of using this line are that establishment of in vitro HIV infection requires relatively few virions and that the infection is chronic rather than lytic, facilitating analysis. For these studies, infection is detected and followed using the ZeptoMetrix HIV p24 Antigen EIA (ZeptoMetrix, Buffalo N.Y.).

CEM cells are cultured in RPMI-1640 containing 10% FBS in 24 well plates Cells are plated at $10^5$ cells per well in a 1 ml volume and 100 ul of various dilutions of virus, either treated or untreated, are added to individual wells. Cultures are fed twice weekly by 50% media replacement and culture supernatants are assayed for HIV p24. All cultures initially contain HIV p24. However, in cultures where virus is noninfectious HIV p24 levels decrease over time eventually reaching background levels. Cultures containing infectious virions exhibit increasing levels of HIV p24 over time allowing easy discrimination of cultures containing infectious versus noninfectious virus. Thus, by comparing the results obtained using different dilutions of virus, one can estimate how many logs of infectious HIV have been inactivated by a given treatment procedure.

Table 1 summarizes data from experiments where purified HIV was treated with different concentrations of paraformaldehyde for 60 minutes. Here, HIV was aliquoted and treated with 0.625%, 1.25%, 2.5% or 5.0% paraformaldehyde. Different dilutions (1:8,000, 1:80,000, and 1:800,000) of treated virus were then placed into cultures of CEM cells and p24 assays were performed on culture supernatants on days 3, 7, 10, and 14 post-inoculation. Data are expressed as pg/ml of HIV p24 protein in the culture supernatants. The standard curve for the p24 assay is linear from 7.8 pg/ml to 125 pg/ml. HIV p24 concentrations below 7.8 pg/ml are expressed as "<7.8 pg/ml" to indicate sensitivity of the assay, and values above 125 pg/ml are expressed as ">125 pg/ml" since the assay is nonlinear above 125 pg/ml.

TABLE 1

Virus Inactivation Using Different Concentrations of Paraformaldehyde

| % Paraformaldehyde | Final Dilution of Treated HIV in Culture | | |
|---|---|---|---|
| | 1:8,000 | 1:80,000 | 1:800,000 |
| A | | | |
| 3 Days Post-Inoculation | | | |
| 0 | 332 pg/ml | 209 pg/ml | 212 pg/ml |
| 0.625 | 71.8 pg/ml | <7.8 pg/ml | <7.8 pg/ml |
| 1.25 | 41.9 pg/ml | <7.8 pg/ml | <7.8 pg/ml |
| 2.5 | <7.8 pg/ml | <7.8 pg/ml | <7.8 pg/ml |
| 5.0 | <7.8 pg/ml | <7.8 pg/ml | <7.8 pg/ml |
| B | | | |
| 7 Days Post-Inoculation | | | |
| 0 | 287 pg/ml | 266 pg/ml | 128 pg/ml |
| 0.625 | 109 pg/ml | <7.8 pg/ml | <7.8 pg/ml |
| 1.25 | 34.2 pg/ml | <7.8 pg/ml | <7.8 pg/ml |
| 2.5 | <7.8 pg/ml | <7.8 pg/ml | <7.8 pg/ml |
| 5.0 | <7.8 pg/ml | <7.8 pg/ml | <7.8 pg/ml |
| C | | | |
| 10 Days Post-Inoculation | | | |
| 0 | 368 pg/ml | 278 pg/ml | 32 pg/ml |
| 0.625 | 22.9 pg/ml | <7.8 pg/ml | <7.8 pg/ml |
| 1.25 | <7.8 pg/ml | <7.8 pg/ml | <7.8 pg/ml |
| 2.5 | <7.8 pg/ml | <7.8 pg/ml | <7.8 pg/ml |
| 5.0 | <7.8 pg/ml | <7.8 pg/ml | <7.8 pg/ml |
| D | | | |
| 14 Days Post-Inoculation | | | |
| 0 | 276 pg/ml | 275 pg/ml | 52 pg/ml |
| 0.625 | <7.8 pg/ml | <7.8 pg/ml | <7.8 pg/ml |
| 1.25 | <7.8 pg/ml | <7.8 pg/ml | <7.8 pgml |
| 2.5 | <7.8 pg/ml | <7.8 pg/ml | <7.8 pg/ml |
| 5.0 | <7.8 pg/ml | <7.8 pg/ml | <7.8 pg/ml |

Untreated virus grew in all cultures at all dilutions tested as evidenced by the presence of HIV p24 in all cultures during the 14 day period. On the other hand, treatment of virus with paraformaldehyde resulted in non-detectable amounts of p24 in the culture supernatants by day 14. Levels of the HIV p24 Ag that could be detected on days 3, 7 and 10 were due to addition of inactivated virus to the cultures as evidenced by a progressive decline in these levels over the 14 day period. Table 2 shows the effects of inactivation methods of this invention according to the exposure time in minutes that the virus is incubated with the crosslinker.

TABLE 2

Virus Inactivation at Different Exposure Times

| Exposure Time | Final Dilution of Treated HIV in Culture | | |
|---|---|---|---|
| | 1:8,000 | 1:80,000 | 1:800,000 |
| A | | | |
| 3 Days Post-Inoculation | | | |
| 0 | >125 pg/ml | >125 pg/ml | >125 pg/ml |
| 15 minutes | >125 pg/ml | 27.9 pg/ml | <7.8 pg/ml |
| 30 minutes | >125 pg/ml | 22.6 pg/ml | <7.8 pg/ml |
| 60 minutes | >125 pg/ml | 59.8 pg/ml | <7.8 pg/ml |
| Overnight | >125 pg/ml | 16.3 pg/ml | <7.8 pg/ml |
| B | | | |
| 7 Days Post-Inoculation | | | |
| 0 | >125 pg/ml | >125 pg/ml | >125 pg/ml |
| 15 minutes | >125 pg/ml | 18.0 pg/ml | <7.8 pg/ml |
| 30 minutes | >125 pg/ml | 10.3 pg/ml | <7.8 pg/ml |
| 60 minutes | >125 pg/ml | 36.0 pg/ml | <7.8 pg/ml |
| Overnight | >125 pg/ml | 17.5 pg/ml | <7.8 pg/ml |
| C | | | |
| 10 Days Post-Inoculation | | | |
| 0 | >125 pg/ml | >125 pg/ml | 32 pg/ml |
| 15 minutes | 43.9 pg/ml | <7.8 pg/ml | <7.8 pg/ml |
| 30 minutes | 46.2 pg/ml | <7.8 pg/ml | <7.8 pg/ml |
| 60 minutes | 87.4 pg/ml | <7.8 pg/ml | <7.8 pg/ml |
| Overnight | 27.6 pg/ml | <7.8 pg/ml | <7.8 pg/ml |
| D | | | |
| 14 Days Post-Inoculation | | | |
| 0 | >125 pg/ml | >125 pg/ml | 52 pg/ml |
| 15 minutes | <7.8 pg/ml | <7.8 pg/ml | <7.8 pg/ml |
| 30 minutes | <7.8 pg/ml | <7.8 pg/ml | <7.8 pg/ml |
| 60 minutes | <7.8 pg/ml | <7.8 pg/ml | <7.8 pg/ml |
| Overnight | <7.8 pg/ml | <7.8 pg/ml | <7.8 pg/ml |

EXAMPLE 4

This example provides a method of preparing the control material of the invention by enzyme digestion of surface proteins. Purified virus (for example, produced as in Example 1) is incubated for approximately 2 hours at 37° C. in a mixture comprising 0.25% bovine trypsin and 0.1% EDTA in Hank's Buffered Saline Solution. At the end of the incubation, the reaction is stopped by adding an equal volume of fetal bovine serum. The material is then purified according to known techniques and non-pathogenicity is confirmed by methods as set out in Example 3.

EXAMPLE 5

This example demonstrates that the viral nucleic acids are intact so as to be amenable to amplification following the inactivation procedures described in Example 3. As an illustration, experiments were conducted to examine whether chemically inactivated HIV could still be detected by PCR. The COBAS AmpliScreen HIV-1 Monitor assay (Roche), a PCR based clinical kit that quantitates HIV RNA copy number, was used. These experiments were performed by titrating material from the inactivation reactions described in Example 3 into a stabilized plasma formulation and then dispensing it into DNAse, RNAse, and pyrogen free PCR tubes (Chasma Scientific, Cambridge, Mass.). Quantitation of HIV RNA copy number was determined on samples of the deep frozen virus using the Roche COBAS assay. Samples were diluted 1:1000 and data is expressed as the copy number at this dilution. This data is summarized in Table 3 below.

TABLE 3

| Paraformaldehyde conc. | HIV RNA copy no. |
| --- | --- |
| 0.63% | 325,000 |
| 1.25% | 48,000 |
| 2.50% | 12,678 |
| 5.00% | 7,192 |

EXAMPLE 6

Several crosslinking reagents were tested for their efficacy in inactivating HIV at various concentrations. Table 4 lists the materials used in the experiments, their concentration, volume, molecular weight and mass.

TABLE 4

| Materials | Concentration | Volume (mL) | Molecular Weight | Mass |
| --- | --- | --- | --- | --- |
| DMA-PBS | 20 mM | 10 | 245.15 | 49 mg |
| BMB-DMSO | 20 mM | 10 | 248.23 | 49.6 mg |
| BMPH-PBS | 40 mM | 2 | 297.19 | 23.7 mg |
| EDC-MES | | 10 | | 10 g |
| Sodium Periodate | 100 mM | 10 | 213.9 | 213 mg |
| Desalting columns | PD-10 | | | |
| MES Buffer | As per packet | | | |
| PBS Buffer | as per packet | | | |
| Glycine | 0.5 M | 10 | 75.07 | 375 mg |
| DMSO | Neat | | | |
| DMF | Neat | | | |

To prepare the HIV buffer pre dilutions, the live HIV is thawed and set on ice. In one dilution, 0.5 mL of HIV is added to 20 mL of PBS buffer, then gently mixed and stored on ice. In another dilution, 0.5 mL of HIV is added to 20 mL of MES buffer, then gently mixed and stored on ice.

For the crosslinking reaction, HIV was combined with one of the crosslinking reagents and/or diluent (PBS or MES) as per Tables 5 (for DMA samples) and 6 (for BMB samples) and mixed gently at room temperature (x,y,z rotator) for 2 hours. The reaction was quenched by addition of 0.5 mL (0.5 M) of glycine, where indicated in Tables 5 and 6, for 1 hour at RT. Then 2.4 mL reaction mixture was added to PD-10 Desalting column (preequilibrated with saline). The virus was eluted with 3.5 mL of saline.

TABLE 5

| Sample | DMA Conc. PBS | DMA Volume mL | Diluted HIV Virus mL | Glycine Quench mL |
| --- | --- | --- | --- | --- |
| 1 | 0.02 mM | 1 | 1 | 0.5 |
| 2 | 0.2 mM | 1 | 1 | 0.5 |
| 3 | 2 mM | 1 | 1 | 0.5 |
| 4 | 20 mM | 1 | 1 | 0.5 |

TABLE 6

| Sample | DMA Conc. in DMSO (mM) | BMB Volume (uL) | Diluent PBS (uL) | Diluted HIV (mL) | Glycine Quench mL |
| --- | --- | --- | --- | --- | --- |
| 5 | 1 | 200 | 800 | 1 | 0.5 |
| 6 | 2.5 | 200 | 800 | 1 | 0.5 |
| 7 | 5 | 200 | 800 | 1 | 0.5 |
| 8 | 20 | 200 | 800 | 1 | 0.5 |

For cross linking with BMPH, the HIV was first pre-treated with Na Periodate to oxidize carbohydrates. Na Periodate and HIV are combined and incubated in the dark for 30 minutes. To crosslink with BMPH, BMPH is added to the pre-treated HIV and mixed gently at RT for 2 hours. The reaction was quenched by addition of 0.5 mL (0.5 M) of glycine. Incubate for 1 hour at RT. Add 2.5 mL of reaction mixture to Desalting column, eluted with 3.5 mL of saline, then aliquoted into 0.5 mL fractions. HIV was diluted 1:10 with defibrinated plasma pool. Table 7 lists the materials and quantities tested.

TABLE 7

| Sample | Na Periodate (100 mM) (uL) | Diluted HIV Virus (mL) | BMPH PBS (mM) | BMPH Volume (mL) | Glycine Quench mL |
| --- | --- | --- | --- | --- | --- |
| 9 | 100 | 1 | 2 | 0.9 | 0.5 |
| 10 | 100 | 1 | 10 | 0.9 | 0.5 |
| 11 | 100 | 1 | 20 | 0.9 | 0.5 |
| 12 | 100 | 1 | 40 | 0.9 | 0.5 |

For crosslinking with EDC, HIV is combined with glycine and mixed for 2 minutes. EDC is added to water, titrated, then 900 uL was added to the reaction mixture, and incubated for 2 hours at RT. The reaction mixture was purified over desalting columns, eluted with 3.5 mL of saline, then aliquoted into 0.5 mL fractions. HIV was diluted 1:10 with defibrinated plasma pool. Table 8 lists the materials and quantities tested.

TABLE 8

| Sample | Glycine 0.5 M | Diluted HIV (mL) | EDC H20 (mg) | EDC Volume (mL) |
| --- | --- | --- | --- | --- |
| 13 | 100 uL | 1 | 0.1 | 0.9 |
| 14 | 100 uL | 1 | 1 | 0.9 |
| 15 | 100 uL | 1 | 10 | 0.9 |
| 16 | 100 uL | 1 | 100 | 0.9 |

The control materials thus produced were tested in the Roche Cobas HIV-1 Monitor Assay described in Example 5. Results are described in Table 9.

TABLE 9

| Sample ID# | Coupling Reagent | Functional Group Structure | Coupling Chemical Reactive Group | Protein Group Reactivity | Concentration mM | Roche Monitor HIV RNA cp/mL (1:10 in *NHP) |
| --- | --- | --- | --- | --- | --- | --- |
| 1 | DMA | Ho | I | —$NH_2$ (Amine) | 0.02 | >7.5 × 105 |
| 2 | DMA | Ho | I | —$NH_2$ (Amine) | 0.2 | >7.5 × 105 |
| 3 | DMA | Ho | I | —$NH_2$ (Amine) | 2 | >7.5 × 105 |
| 4 | DMA | Ho | I | —$NH_2$ (Amine) | 20 | >7.5 × 105 |

TABLE 9-continued

| Sample ID# | Coupling Reagent | Functional Group Structure | Coupling Chemical Reactive Group | Protein Group Reactivity | Concentration mM | Roche Monitor HIV RNA cp/mL (1:10 in *NHP) |
|---|---|---|---|---|---|---|
| 5 | BMB | Ho | M | SH | 1 | Negative |
| 6 | BMB | Ho | M | SH | 2.5 | Negative |
| 7 | BMB | Ho | M | SH | 5 | Negative |
| 8 | BMB | Ho | M | SH | 20 | $1.6 \times 10^5$ |
| 9 | BMPH | He | M + H | SH + CO | 2 | $>7.5 \times 10^5$ |
| 10 | BMPH | He | M + H | SH + CO | 10 | $1.29 \times 10^4$ |
| 11 | BMPH | He | M + H | SH + CO | 20 | $3.61 \times 10^3$ |
| 12 | BMPH | He | M + H | SH + CO | 40 | $5.58 \times 10^2$ |
| 13 | EDC | Ho | C | —COOH + NH2 groups | 0.1 (mg/mL) | $>7.5 \times 10^5$ |
| 14 | EDC | Ho | C | —COOH + NH2 groups | 1 (mg/mL) | $>7.5 \times 10^5$ |
| 15 | EDC | Ho | C | —COOH + NH2 groups | 10 (mg/mL) | $>7.5 \times 10^5$ |
| 16 | EDC | Ho | C | —COOH + NH2 groups | 100 (mg/mL) | $>7.5 \times 10^5$ |

*Roche Cobas HIV-1 Monitor Assay (Range 400-750,000 cp/mL)
**NHP = defibrinated normal human plasma
He—Heterobifunctional
Ho—homobifunctional
I—imidoester
M—maleimide
H—hydrizide
C—carbodiimide
SH—sulfhydryl
CO—carbonyl (aldehyde)

EXAMPLE 7

Inactivation of Hepatitis B Virus

In this example the method of the invention is applied to inactivation of the hepatitis B virus using paraformaldehyde. Purified virus, prepared as described herein, was inactivated using the method described in Example 2. Duck hepatitis B virus (DHBV) was employed as surrogate to human hepatitis B virus (HHBV) in HBV inactivation studies as ethical concerns, availability and cost limit the use of chimpanzee in hBV inactivation studies. This model uses primary duck hepatocytes (PDHs) as host (Pugh et al., 1999). We isolated and maintained PDHs from less than one week-old seronegative White Pekin ducklings (*Anas dornesticus*) with modifications from previous procedures (Berry and Friend, 1969, Seglen. 1976, Pugh and Summers, 1989, Pugh et al., 2000, Tuttleman et al., 1986). Briefly, ducks were euthanized by exposing them to $CO_2$ and livers were perfused twice via the atrium of the heart with approximately 200 mL each of two solutions. The first solution consisted of SWIM's S-77 medium (Sigma) supplemented with 0.5 mmol/L EGTA, 2 mmol/L Hepes (pH 7.45) and 50 ug/mL penicillin and streptomycin (Biofluids, Rockville, Md.). The second solution contained SWIM's S-77 medium supplemented with 2.5 mmol/L $CaCl_2$, 0.5 mg of collagenase/mL (type I, Sigma, St. Louis) and 50 ug/mL penicillin and streptomycin. These perfusates were administered at approximately 15 mL/minute using a peristaltic pump and the temperature of the perfusate was adjusted to maintain the liver at 37° C. The liver was removed, minced with scissors and repeatedly mixed with a 25 mL pipette for hepatocyte dispersion into complete L-15 medium (Biofluids, Rockville, Md.) supplemented with 0.05-percent (w/v) sodium bicarbonate (Biofluids), 1 mmol/L glutamine (Biofluids), 20 mmol/L HEPES (Biofluids), 50 ug/mL penicillin and streptomycin (Biofluids), I (g/mL insulin (Sigma, St. Louis), and 10 (moi/L hydrocortisone-hemisuccinate (Sigma). Cells were filtered through sterile gauze, centrifuged at 50×g for 4 minutes, and the resulting cell pellet was washed three times with L-15 medium and resuspended in L-15 medium. 12-well plates were seeded with approximately two-mL of the cell suspension (ca. 105 cells). Media on the plated cells were aspirated every two days and replaced with fresh L-15 media.

Serum of four week-old congenitally infected duckling served as the source of virus used in these experiments. Treated and control DHBV spiked red cell samples were serially diluted 10-fold in L-15 medium and one-mL volumes were subsequently inoculated into PDH monolayers in quadruplicate. The infected cultures were incubated at 37° C.+20° C. with 5+1% $CO_2$ overnight for virus attachment and entry. The inoculum was then removed, cell monolayers washed once with complete L-15 medium to remove excess red blood cells, and then each well was overlaid with approximately 2-mL of fresh L-15 medium. Infected monolayers were incubated an additional 10-14 days at 37(+20° C. with 5+1% $CO_2$, with media changes every 2 days.

We detected the presence of DHB V-infected duck hepatocytes by an IFA. Briefly, the medium from the PDH monolayer was removed by aspiration, and the monolayers washed with agitation for 5-10 minutes with 1-2 mL of phosphate buffered saline (PBS). The wash solution was then removed by aspiration and replaced with 1-2 mL of –20+2° C. ethanol. The ethanol overlaid samples were fixed for 2-48 hours at 4+1° C. prior to removal of the ethanol, and subsequent to a 1-2 mL PBS wash, agitated monolayers were incubated at room temperature for at least 2 hours with 0.25 mL of a 1:2 dilution of anti-DHBV monoclonal antibody directed against pre-S domain of DHVB envelope (1 H. 1) (Pugh et al., 1995) in PBS containing 0.5% fetal bovine serum to each well. The antibody solution was removed by aspiration, and the primary antibody stained monolayer washed with PBS. Following removal of the wash, 0.25 mL of a 1:200 dilution of goat anti-Mouse IgG-FITC (fluorescein isothiocyanate conjugate) (Jackson ImmnuroResearch Laboratories, Inc., West Grove. Pa.), in PBS containing 0.5% fetal bovine serum was added to each well and incubated with agitation for 2 hours at room temperature. The secondary antibodies were removed by aspiration, and the fluorescently-stained monolayer washed with PBS. Following removal of the PBS, inverted wells were examined by UV light microscopy using a Nikon Diaphot microscope, arid monolayers that contained one or more DHBV surface antigen positive hepatocytes were scored positive. Virus titers were determined by scouring fluorescence focus-forming unit dose 50 using Reed and Muench method (1938).

As shown in Table 10, no virus infected cells were detected in any of the samples tested.

TABLE 10

Effect of paraformaldehyde on inactivation of duck hepatitis B virus (DHBV) in suspension for 60 minutes at ambient room temperature (20° C.).

| Dilution | Input virus | Paraformaldehyde/FFFUs observed in dilutions assayed | | | |
|---|---|---|---|---|---|
| | | 1 | 2 | 3 | 4 |
| $10^{-1}$ | ++++ | ---- | ---- | ---- | ---- |
| $10^{-2}$ | ++++ | ---- | ---- | ---- | ---- |
| $10^{-3}$ | ++++ | ---- | ---- | ---- | ---- |
| $10^{-4}$ | ++++ | ---- | ---- | ---- | ---- |
| $10^{-5}$ | ++++ | ---- | ---- | ---- | ---- |
| $10^{-6}$ | ++-- | ---- | ---- | ---- | ---- |
| $10^{-7}$ | ---- | ---- | ---- | ---- | ---- |
| *FFFUD$_{50}$/mL ($\log_{10}$) | $10^{6.00}$ | 0 | 0 | 0 | 0 |

*FFFUD$_{50}$/ML = Fluorescence focus forming unit dose fifty as determined by Reed and Muench (1938). (+) presence or (−) absence of FFFU.
+, DHBV infected cells detected; −, no DHBV infected cells detected.

EXAMPLE 8

Inactivation of Bovine Viral Diarrhea Virus (BVDV)

In this example bovine viral diarrhea virus (BVDV), biotype 1 (CPE), genotype 1 Host: Madin-Darby bovine kidney (MDBK) cells were inactivated according to the methods discussed in Example 2.

Bovine viral diarrhea virus (BVDV), biotype 1 (CPE), genotype 1 was used in these studies which infect Madin-Darby bovine kidney (MDBK) cells. The procedure for assaying infectious BVDV was the same as described for DHBV (see above) with the following differences: post-treatment of both test and control BVDV samples with 2.5% paraformaldehyde, the reaction was quenched with 0.5 M glycine. These samples (0.5 mL) were loaded into pre-spun sephacryl columns. The columns were spun for 4 minutes at 1000 rpm. The samples were aseptically removed from the columns and ten-fold serial dilutions were then prepared in minimal essential medium (MEM) and adsorbed on the monolayer of host cells seeded in tissue culture plates for one hour at 37±2° C. and 5+1% $CO_2$. Post-adsorption, the monolayers were washed with EBSS and replaced with fresh MEM and incubated for 5-7 days at 37±2° C. and 5±1% $CO_2$. The presence of infectious viruses was determined as described below: post-incubation, the plates were washed with 3× with PBS and fixed with TC grade alcohol and stained with direct porcine polyclonal anti-BVDV conjugated antibody. The stained plate were scored using UV microscopy using a Nikon Diaphot microscope, and monolayers that contained one or more BVDV surface antigen positive hepatocytes were scored positive. Four wells per dilution were inoculated and results were recorded as the FFFUD$_{50}$ calculated by Reed and Munch (1938).

As shown in Table 11, no virus infected cells were detected in any of the samples tested.

TABLE 11

Effect of paraformaldehyde on inactivation of bovine viral diarrhea virus (BVDV) in suspension for 60 minutes at ambient room temperature (20° C.).

| Dilution | Input virus | Paraformaldehyde/FFFUs observed in dilutions assayed | | | |
|---|---|---|---|---|---|
| | | 1 | 2 | 3 | 4 |
| $10^{-1}$ | ++++ | ---- | ---- | ---- | ---- |
| $10^{-2}$ | ++++ | ---- | ---- | ---- | ---- |
| $10^{-3}$ | ++++ | ---- | ---- | ---- | ---- |
| $10^{-4}$ | ++++ | ---- | ---- | ---- | ---- |
| $10^{-5}$ | ++++ | ---- | ---- | ---- | ---- |
| $10^{-6}$ | ++-- | ---- | ---- | ---- | ---- |
| $10^{-7}$ | ---- | ---- | ---- | ---- | ---- |
| *FFFUD$_{50}$/mL ($\log_{10}$) | $10^{6.77}$ | 0 | 0 | 0 | 0 |

*FFFUD$_{50}$/ML = Fluorescence focus forming unit dose fifty as determined by Reed and Muench (1938). (+) presence or (−) absence of FFFU.
Table Footnote: +, BVDV infected cells detected; −, no BVDV infected cells detected.

References

Pugh J C, Summers J W. Infection and uptake of duck hepatitis B virus by duck hepatocytes maintained in the presence of dimethyl sulfoxide. Virology 1989; 172:564.572.

Pugh, J. C., Ijaz, M. K., Suchmann D. B. Use of surrogate models for testing efficacy of disinfectants against Hepatitis B virus. Am J Infect Cont 1999; 27:373-6. Pugh, J. C., Suchmann, D. B., Ijaz, M. K. Hepatitis B virus efficacy testing: Qualification of an avian Hepadavirus in vitro system that uses primary duck hepatocyte cultures. 10th International Symposium on Viral Hepatitis and Liver Diseases. Atlanta. USA, 2000, Abstract B 139.

Berry, M. N., Friend, D. S. High-yield preparation of isolated rat liver parenchymal cells. J. Cell Biology 1969; 43:506-520.

Seglen, P. Preparation of isolated rat liver cells. Methods Cell Biol 1971; 3:29-83.

Pugh, J. C., Di, Q. U., Mason W. S., Simmons H. Susceptibility to duck hepatitis B virus infection is associated with the presence of cell surface receptor sites that efficiently bind virus particles. J Virol 1995; 69:4814-22.

Reed, L., Muench, H. A. A simple method of estimating fifty percent end points. Am J of Hyg 1938; 27:493-497.

It should be understood that while the invention has been described in detail herein, the examples provided are for illustrative purposes only. Other modifications of the embodiments of the present invention that are obvious to those of ordinary skill in the art are intended to be within the scope of the invention, which is more fully defined in the claims which follow hereafter.

What is claimed is:

1. A method for detection of a microorganism in a biological test sample comprising: a) providing a biological fluid test sample suspected of comprising the microorganism; b) providing a positive control sample comprising the microorganism in a biological fluid corresponding to the biological fluid of the test sample, wherein the positive control sample is prepared by exposing a purified microorganism to an aldehyde at a temperature of 2-8° C., and quenching the aldehyde exposed microorganism with glycine for at least 2 hours such that the microorganism is in an intact, non-pathogenic, form in which one or more of the surface proteins have been irreversibly modified by covalent attachment to the aldehyde and wherein the nuclear components are substantially intact; c) processing the test and the positive control sample to extract the nuclear components of the microorganisms; d) amplifying the nuclear components of the microorganisms in the test sample and the positive control; and e) comparing the results of nucleic acid amplification in the test sample and the positive control to identify the presence of microorganisms in the test sample.

2. The method of claim 1, wherein the aldehyde comprises a single reactive functional group.

3. The method of claim 2, wherein the aldehyde is selected from the group consisting of paraformaldehyde, formaldehyde, acetaldehyde, propionaldehyde, n-butyraldehyde, benzaldehyde, p-nitrobenzaldehyde, p-tolualdehyde, salicylaldehyde, phenylacetaldehyde.

4. The method of claim 1, wherein the aldehyde comprises two or more reactive functional groups.

5. The method of claim 4, wherein the aldehyde is paraformaldehyde.

6. The method of claim 1, wherein the microorganism is a virus.

7. The method claim 6, wherein the virus is chosen from the group consisting of human immunodeficiency virus, hepatitis C virus, hepatitis B virus, cytomegalovirus, human lymphotrophic virus, Epstein-Barr virus, parvovirus, herpes simplex virus, human herpes virus 8 and hepatitis A Virus.

8. The method of claim 1, wherein the microorganism is an intracellular parasite.

9. The method of claim 8, wherein the parasite is chosen from the group consisting of *Chlamydia trachomatis, Chlamydia psittaci, Rickettsia prowazeki, Rickettsia typhi, Rickettsia rickettsi, Rickettsia sibtricus, Rickeitsia conori, Rickettsia australis, Rickettsia akari, Rickettsia tsutsugamushi, Coxiella bumeti* and *Rochalimaea Quintana*.

10. The method of claim 1, wherein the positive control is added to the test sample.

11. The method of claim 1, wherein the biological fluid test sample is selected from the group consisting of serum, plasma, defibrinated plasma, stabilized plasma pool, cerebrospinal fluid, urine, saliva, semen and sputum.

* * * * *